United States Patent [19]

Francis et al.

[11] 4,075,397
[45] Feb. 21, 1978

[54] CELL HAVING CHALCOGENIDE CATHODE AND SOLVATED ALKALI METAL SALT ELECTROLYTE

[75] Inventors: Robert W. Francis, Linden; Gerald H. Newman, Westfield, both of N.J.

[73] Assignee: Exxon Research & Engineering Co., Linden, N.J.

[21] Appl. No.: 773,284

[22] Filed: Mar. 1, 1977

[51] Int. Cl.$^2$ ............................................. H01M 10/44
[52] U.S. Cl. ........................................ 429/50; 429/191
[58] Field of Search ........................... 429/50, 191, 218

[56] References Cited

U.S. PATENT DOCUMENTS

| | | | |
|---|---|---|---|
| 3,977,900 | 8/1976 | Luehrs | 429/191 X |
| 4,009,052 | 2/1977 | Whittingham | 429/191 |

*Primary Examiner*—C. F. LeFevour
*Attorney, Agent, or Firm*—Kenneth P. Glynn

[57] ABSTRACT

A novel electrochemical cell is disclosed utilizing: (a) an anode which contains as the anode-active material an alkali metal, (b) a cathode which contains as the cathode-active material a chalcogenide of the empirical formula $M'A_p$ wherein $M'$ is one or more metals selected from the group consisting of titanium, zirconium, hafnium, niobium, tantalum and vanadium, A is one or more chalcogens selected from the group consisting of oxygen, sulfur, selenium and tellurium, and $p$ is a numerical value between about 1.8 and about 3.2; and (c) a solid electrolyte consisting essentially of one or more solvated metal-alkali metal-halogen compounds of the formula $ZMX_n$ wherein Z is an alkali metal, M is a metal selected from the group consisting of Zn, Cd, B, Al, Ga, In, Tl, Sn (stannous), P and As, and wherein X is one or more halogens selected from the group consisting of chlorine, fluorine, bromine and iodine and $n$ is a numerical value equal to one plus the valence of the metal M. Preferred are the cells wherein the anode is lithium, the cathode contains as its cathode-active material $TiS_2$, and the electrolyte consists essentially of a solid solvated metal-lithium-halogen salt.

13 Claims, No Drawings

CELL HAVING CHALCOGENIDE CATHODE AND SOLVATED ALKALI METAL SALT ELECTROLYTE

BACKGROUND OF THE INVENTION

1. Field of the Invention

This invention relates to a novel electric current producing cell. More particularly, this invention relates to improvements in the electric current producing cells of the type comprising an alkali metal anode, a solid electrolyte, and a cathode having metal chalcogenide cathode-active material.

2. Description of the Prior Art

There has been considerable interest in recent years in developing high energy density electrochemical cell systems. Among the systems being investigated are those employing nonaqueous electrolytes including liquid and fused electrolytes, anodes containing lightweight metals, such as alkali metals, and cathodes containing chalcogenide compounds. Typical systems are described, for example, in U.S. Pat. Nos. 3,988,164; 3,925,098; 3,864,167 and 3,791,867.

Additionally, various efforts have been made to develop solid state electrolytes for high energy density electrochemical cell systems. Alkali metal-aluminum-halogen compounds have been utilized in liquid and molten state electrolyte systems (e.g., as described in U.S. Pat. No. 3,877,984 and U.S. Pat. No. 3,751,298) and solid alkali metal-aluminum-halogen compound conductivity studies have been made (e.g., N. I. Anufrieva et al, *Tseut. Metal.*, Vol. 1, pp 32–36 (1973); W. Weppner et al, *Physics Letters*, Vol. 58A, No. 4, pp 245–248 (1976); and J. Schoonman et al, *J. Solid State Chem.*, Vol. 16, pp 413–422 (1976)). Additionally, some solvent complexed alkali metal salts have been described as solid electrolytes (see U.S. Pat. Nos. 3,704,174 and 3,977,900, for example). However, to date, there has been no suggestion that the solvated metal-alkali metal-halogen compounds of the type employed in the present invention might be useful in solid state electrolyte systems having alkali metal anodes and chalcogenide cathodes.

SUMMARY OF THE INVENTION

A novel electric current-producing cell of the present invention has been developed which contains: (a) an alkali metal-containing anode; (b) a cathode containing metal chalcogenide cathode-active material; and (c) a solid electrolyte consisting essentially of one or more solvated metal-alkali metal-halogen compounds of the formula:

$$ZMX_n$$

wherein Z is an alkali metal, M is a non-alkali type metal more fully described below, X is one or more halogens and n is a numerical value equal to one plus the valence of the metal M.

DETAILED DESCRIPTION OF THE INVENTION

The novel electric current-producing cell of the present invention is a solid state cell which contains an anode, a cathode and a solid electrolyte. By "solid state" is meant a cell from which electric current may be drawn at temperatures below the melting point of a solid electrolyte.

The anode employed in the cell of the present invention is one which contains alkali metal as its active material. Desirably the anode is substantially sodium, potassium, lithium or alloys containing these, and preferably the anode is lithium metal or an alloy of lithium. The anode, e.g., lithium, may be in contact with other metal structures, e.g., nickel, copper or silver screen, which serve as current collectors and are well known in the art.

The cathode used in the cell of the present invention is one which contains as its cathode-active material one or more chalcogenide compounds of the empirical formula:

$$M'A_p \tag{1}$$

wherein M' is one or more metals selected from the group consisting of titanium, zirconium, hafnium, niobium, tantalum and vanadium; A is one or more chalcogens selected from the group consisting of oxygen, sulfur, selenium and tellurium, and p is a numerical value between about 1.8 and about 3.2. Advantageously, M' is titanium in Formula (1) and the titanium dichalcogenides are desirable. Also A in Formula (1) is advantageously sulfur. Thus, the metal sulfides are particularly useful. In the most preferred embodiments, M' is titanium and A is sulfur. Desirably, p is a numerical value between about 1.8 and about 2.1, and preferably between about 1.95 and about 2.02.

The chalcogenides which are used as the cathode-active material may be any of the compounds within the scope of Formula (1) above. Among these are $TiS_2$, $ZrS_2$, $HfS_2$, $NbSe_3$, $TaSe_2$, $TaSe_3$, $TaO_{2.5}$ (or $Ta_2O_5$), $VSe_2$, $VO_{2.5}$ (or $V_2O_5$) and the like. Vanadium disulfide is not known but theoretically it should possess a structure of the type found in the other disclosed dichalcogenides and should be similarly electrochemically active. Disulfides of vanadium in combination with other transition metals, such as $V_{0.25}Ti_{0.75}S_{2.0}$, display the requisite electrochemical activity, as do vanadium diselenide and vanadium ditelluride.

The cathode-active material used in the cathode of the cell of the present invention is preferably an intercalatable compound. It should be noted that intercalated dichalcogenides are such in the discharged state, and that, in the charged state, the intercalatable chalcogenide contains substantially no intercalated species.

The cathode structure itself need not necessarily consist of the cathode-active material alone but may be a structure such as carbon, nickel, zinc, etc., upon which the dichalcogenide is deposited. Preferably, however, the cathode structure consists entirely of the dichalcogenide. The cathode-active material is typically a good electronic conductor and may thus often serve as its own current collector. The cathode-active material may be admixed or diluted with a minor amount of any other electrochemically active material, and alloys (i.e., solid solutions) of the individual chalcogenides may be used as well as the individual chalcogenides. The cathode may be readily fabricated from the individual or alloyed chalcogenides using materials and methods well known in the prior art, e.g., polytetrafluoroethylene bonding agents or support structures such as nickel or copper mesh.

The electrolyte employed in the novel cell of the present invention is a solid electrolyte and consists essentially of one or more solvated compounds of the formula:

$$ZMX_n \qquad (2)$$

wherein Z is an alkali metal, wherein M is a metal selected from the group consisting of Zn, Cd, B, Al, Ga, In, Tl, Sn (stannous), P and As, wherein X is one or more halogens selected from the group consisting of chlorine, fluorine, bromine and iodine, and wherein $n$ is a numerical value equal to one plus the valence of the metal M, and thus represents the number of halogen atoms present, i.e., three, four or six.

Desirably, the alkali metal Z in Formula (2) is selected from the group consisting of sodium, lithium and potassium. Preferred is lithium. The metal M in Formula (2) above is, as mentioned, any of zinc, cadmium, boron, aluminum, gallium, indium, thallium, tin (stannous), phosphorus and arsenic. Desirably, M is selected from the group consisting of boron, aluminum, phosphorus and arsenic. Preferably, M is selected from the group consisting of boron, phosphorus or arsenic.

The halogen X is one or more selected from Cl, F, Br and I, and, therefore, in general, the compounds encompassed by Formula (2) above include those having more than one type of halogen atom, e.g., tetrachlorodibromo compounds of phosphorus and arsenic, dichlorodibromo compounds, trichloroiodo compounds and the like. However, desirably all of the halogen atoms in the compound are the same, i.e., X is a single halogen selected from the group consisting of chlorine, fluorine, bromine and iodine. Preferably X is chlorine or fluorine, particularly fluorine. Among the specific solid electrolyte compounds which are included are: $LiZnCl_3$; $LiPF_6$; $LiAsF_6$; $LiBCl_4$; $LiBBr_4$; $LiBI_4$; $LiAlCl_4$; $LiAlBr_4$; $LiAlI_4$; $LiAlCl_3Br$; $NaAlCl_4$; $NaAlCl_3Br$; $NaAlBr_4$; $NaAlI_4$; $KAlCl_4$; $KAlCl_3Br$ and the like. The most preferred compounds are $LiPF_6$, $LiAsF_6$ and $LiBF_4$, particularly $LiPF_6$.

The electrolyte compound of Formula (2) may be prepared by reacting an alkali metal halide with a metal halide, for example, in solution with the hydrogen halide which corresponds to the alkali metal halide. The reaction may proceed at an acceptable rate at room temperature or may be enhanced by heating. Known techniques may be used to concentrate and/or separate the solid compound, as desired, for subsequent solution. Alternatively, commercially available salts, e.g., anhydrous $LiPF_6$, could be used.

The solvent used in the solvation of the compound represented by Formula (2) above is generally an ether. Among the ethers which are useful are the unsubstituted and inertly substituted monoethers and polyethers. By "inertly substituted" ether is meant an ether containing substituents which have no detrimental effect on the solvation of the Formula (2) compound or on its use as an electrolyte. These ethers include dimethoxyethane (DME), 2-methoxyethyl ether (diglyme), triethylene glycol dimethyl ether (triglyme) and the like. Preferred is dimethoxyethane.

The metal-alkali metal-halogen compounds of the above formula are solvated with one or more solvents, as mentioned, by dissolving the compound in the desired solvent. The excess solvent is subsequently removed by known techniques, e.g., by vacuum, to yield the solid solvated electrolyte salt. For example, the solvated salt compounds may be formed by dissolving an anhydrous salt of the Formula (2) type, above, in pure solvent. It is useful, although not critical, to predry the salt prior to dissolving it in the solvent, e.g., by vacuum drying at an elevated temperature. Sufficient salt may be dissolved so as to obtain appreciable solvated salt product, and there is otherwise no criticality to the amount dissolved. As a practical matter, sufficient salt should be used to render the process economically attractive. There is no upper limit to the amount of salt dissolved into the solvent, except that amounts over the saturation level of the solvent will not necessarily be solvated. Of course, as solvated salt is formed in a given solution, more salt may be added to enhance further solvated salt production. In a preferred technique, sufficient salt is added to heated solvent so that the solution becomes saturated and the solution is then cooled to precipitate out solvated salt product. The solvated product may be separated by filtering, washed with an inert solvent, e.g., benzene, to remove excess solvent and/or vacuum dried with heat. Other techniques for obtaining the solid solvated salt electrolyte will be apparent to the artisan.

The solid solvated alkali metal salt electrolyte is subsequently formed into the desired shape by molding, pressing, rolling, binding with polymeric compounds which do not detrimentally affect the electrolytic activity of the electrolyte. In one embodiment, the electrolyte is rolled into or pressed into a thin sheet of about 10 mils or less. In another embodiment, the solid electrolyte may be melted and then cooled to form a glassy solid sheet. In any event, the electrolyte consisting essentially of one or more solvated Formula (2) type compounds may be formed into known solid electrolyte configurations for use in the electrochemical cell.

The present invention is illustrated by the following examples, but the invention should not be construed as being limited thereto.

EXAMPLE 1

A solid state electrolyte consisting of dimethoxyethane solvated $LiPF_6$ was prepared for testing. Commercially obtained anhydrous $LiPF_6$ was dissolved in dimethoxyethane until a saturated solution was formed. The solvated $LiPF_6$ salt was immediately formed and the excess dimethoxyethane was removed by vacuum to yield a solid electrolyte composition.

EXAMPLE 2

The solid state electrolyte prepared in accordance with Example 1 above was used in a test cell as follows:

The solid electrolyte having a diameter of about 1.0 cm and about 0.3 cm thick, was sandwiched between an 0.5 cm thick lithium metal anode of about the same diameter and an 0.5 cm thick pressed $TiS_2$ powder cathode of approximately the same diameter. An open current voltage of about 2.5 volts was observed. Upon discharge, the current drain through the battery measured by a high impedance electrometer was about 1 to $10\mu$ amps across the electrolyte pellet. The full cell voltage was determined to be about 2.0 volts upon initial discharge.

What is claimed is:

1. An electric current-producing cell, comprising:
   a. an alkali metal-containing anode;
   b. a cathode containing as its cathode active material, one or more chalcogenides of the empirical formula:

$$M'A_p$$

wherein M' is one or more metals selected from the group consisting of titanium, zirconium, hafnium, niobium, tantalum and vanadium, wherein A is one or more chalcogens selected from the group consisting of oxygen, sulfur, selenium and tellurium, and wherein $p$ is a numerical value between about 1.8 and about 3.2; and c. a solid electrolyte consisting essentially of one or more solvated compounds of the formula:

$$ZMX_n$$

wherein Z is an alkali metal, wherein M is a metal selected from the group consisting of Zn, Cd, B, Al, Ga, In, Tl, Sn (stannous), P and As, wherein X is one or more halogens selected from the group consisting of chlorine, fluorine, bromine and iodine, and wherein $n$ is a numerical value equal to one plus the valence of the metal M, said compounds having been solvated with one or more solvents selected from the group consisting of unsubstituted and inertly substituted monoethers and polyethers.

2. The cell of claim 1 wherein the anode is substantially sodium, lithium, potassium or alloys containing these and wherein Z is selected from the group consisting of sodium, lithium and potassium.

3. The cell of claim 2 wherein A is sulfur and wherein M is selected from the group consisting of B, Al, P and As.

4. The cell of claim 1 wherein M' is titanium and X is selected from the group consisting of chlorine and fluorine.

5. The cell of claim 4 wherein A is sulfur.

6. The cell of claim 5 wherein the anode is substantially lithium or a lithium alloy wherein Z is lithium, wherein M is selected from the group consisting of B, Al, P and As.

7. The cell of claim 6 wherein X is selected from the group consisting of chlorine and fluorine.

8. An electric current-producing cell comprising:
a. a lithium metal-containing anode;
b. a cathode containing titanium disulfide as the cathode-active material; and
c. a solid electrolyte consisting essentially of ether solvated $LiPF_6$.

9. The cell of claim 8 wherein the solvated $LiPF_6$ has been solvated with dimethoxyethane.

10. A method of operating an electric current-producing cell, comprising:

drawing a current from the cell at a temperature below the melting point of the electrolyte of the cell, wherein the cell contains:
a. an alkali metal-containing anode;
b. a cathode containing as its cathode-active material, one or more chalcogenides of the empirical formula:

$$M'A_p$$

wherein M' is one or more metals selected from the group consisting of titanium, zirconium, hafnium, niobium, tantalum and vanadium, wherein A is one or more chalcogens selected from the group consisting of oxygen, sulfur, selenium and tellurium, and wherein $p$ is a numerical value between about 1.8 and about 3.2; and c. a solid electrolyte consisting essentially of one or more solvated compounds of the formula:

$$ZMX_n$$

wherein Z is an alkali metal, wherein M is a metal selected from the group consisting of Zn, Cd, B, Al, Ga, In, Tl, Sn (stannous), P and As, wherein X is one or more halogens selected from the group consisting of chlorine, fluorine, bromine and iodine, and wherein $n$ is a numerical value equal to one plus the valence of the metal M, said compounds having been solvated with one or more solvents selected from the group consisting of unsubstituted and inertly substituted monoethers and polyethers.

11. The method of claim 10 wherein the anode is substantially sodium, lithium, potassium, or alloys containing these, wherein A is sulfur, and wherein Z is selected from the group consisting of sodium, lithium and potassium and wherein X is selected from the group consisting of chlorine and fluorine.

12. The method of claim 11 wherein the anode is substantially lithium or a lithium alloy, wherein Z is lithium and wherein M is selected from the group consisting of B, Al, P and As.

13. The method of claim 12 wherein the cathode-active material is titanium disulfide, and wherein the solid electrolyte consists essentially of ether solvated $LiPF_6$.

* * * * *